United States Patent
Abe et al.

(10) Patent No.: US 11,690,561 B2
(45) Date of Patent: Jul. 4, 2023

(54) COGNITIVE FUNCTION EVALUATION SYSTEM

(71) Applicant: Panasonic Intellectual Property Management Co., Ltd., Osaka (JP)

(72) Inventors: Kengo Abe, Nara (JP); Takashi Nishiyama, Hyogo (JP); Hirobumi Nakajima, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 359 days.

(21) Appl. No.: 16/977,056

(22) PCT Filed: Feb. 26, 2019

(86) PCT No.: PCT/JP2019/007197
§ 371 (c)(1),
(2) Date: Aug. 31, 2020

(87) PCT Pub. No.: WO2019/172012
PCT Pub. Date: Sep. 12, 2019

(65) Prior Publication Data
US 2021/0045673 A1  Feb. 18, 2021

(30) Foreign Application Priority Data
Mar. 9, 2018  (JP) ................. 2018-042953

(51) Int. Cl.
*A61B 5/00* (2006.01)
*A61B 5/05* (2021.01)
*A61B 5/11* (2006.01)

(52) U.S. Cl.
CPC .............. *A61B 5/4088* (2013.01); *A61B 5/05* (2013.01); *A61B 5/1115* (2013.01); *A61B 5/1118* (2013.01)

(58) Field of Classification Search
CPC ....... A61B 5/4088; A61B 5/05; A61B 5/1115; A61B 5/1118; A61B 5/0507; A61B 5/1123; A61B 5/6889; A61B 5/6892; A61B 10/00
See application file for complete search history.

(56) References Cited

U.S. PATENT DOCUMENTS

2014/0240121 A1  8/2014  Yasukawa
2016/0077123 A1  3/2016  Kagaya
(Continued)

FOREIGN PATENT DOCUMENTS

JP  2001-76272 A  3/2001
JP  2009-098098 A  5/2009
(Continued)

OTHER PUBLICATIONS

International Search Report for corresponding Application No. PCT/JP2019/007197, dated May 21, 2019.
(Continued)

*Primary Examiner* — Eric F Winakur
*Assistant Examiner* — Jonathan Drew Moroneso
(74) *Attorney, Agent, or Firm* — Renner, Otto, Boisselle & Sklar, LLP

(57) ABSTRACT

An estimation system includes: a first sensor that detects a first amount of activity that is an amount of activity of a subject in a room; a second sensor that detects a second amount of activity that is an amount of activity of the subject on a bed in the room; and an estimation device that estimates at least one of a position and an action of the subject in association with a position in the room based on the first amount of activity detected by the first sensor and the second amount of activity detected by the second sensor, and outputs an estimation result obtained from the estimation.
(Continued)

The first sensor and the second sensor are sensors other than two-dimensional image sensors.

4 Claims, 10 Drawing Sheets

(56) References Cited

U.S. PATENT DOCUMENTS

| | | | |
|---|---|---|---|
| 2016/0371593 A1* | 12/2016 | Nishiyama | ......... G08B 21/0423 |
| 2018/0122209 A1* | 5/2018 | Jefferson | .............. A61B 5/0015 |
| 2019/0231246 A1 | 8/2019 | Nishiyama | |
| 2020/0066130 A1* | 2/2020 | Ten Kate | ................ G06F 3/017 |

FOREIGN PATENT DOCUMENTS

| | | |
|---|---|---|
| JP | 2010-133692 A | 6/2010 |
| JP | 2013-170848 A | 9/2013 |
| JP | 2014-38667 A | 2/2014 |
| JP | 2014-166196 A | 9/2014 |
| JP | 5648840 B | 1/2015 |
| JP | 2016-19584 A | 2/2016 |
| JP | 2016-59458 A | 4/2016 |
| JP | 2016-218773 A | 12/2016 |
| JP | 2017-104289 A | 6/2017 |
| JP | 2017-117423 A | 6/2017 |
| JP | 2017-168098 A | 9/2017 |
| WO | 2017/154805 A1 | 9/2017 |

OTHER PUBLICATIONS

Written Opinion for corresponding Application No. PCT/JP2019/007197, dated May 21, 2019.

* cited by examiner

FIG 5B

| LABEL | LOCATION | ACTION |
|---|---|---|
| 1 | OUTSIDE OF ROOM | STILL |
| 2 | OUTSIDE OF ROOM | MAKE MOVEMENT |
| 3 | OUTSIDE OF ROOM → INSIDE OF ROOM | ENTER ROOM |
| 4 | INSIDE OF ROOM | MOVE LONG DISTANCE FROM SENSOR |
| 5 | INSIDE OF ROOM | MOVE SHORT DISTANCE FROM SENSOR |
| 6 | INSIDE OF ROOM | WALK SLOWLY |
| 7 | INSIDE OF ROOM → BED | GET INTO BED |
| 8 | BED | LIE FACE UP |
| 9 | BED | LIE ON SIDE |
| 10 | BED | LIE FACE DOWN |
| 11 | BED | LIE FACE UP |
| 12 | BED | MOVE SLIGHTLY |
| 13 | BED | TURN OVER |
| 14 | BED | GET UP ON BED |
| 15 | BED | SIT ON BED |
| 16 | BED | SIT STILL ON BED |
| 17 | BED → INSIDE OF ROOM | GET OFF FROM BED |

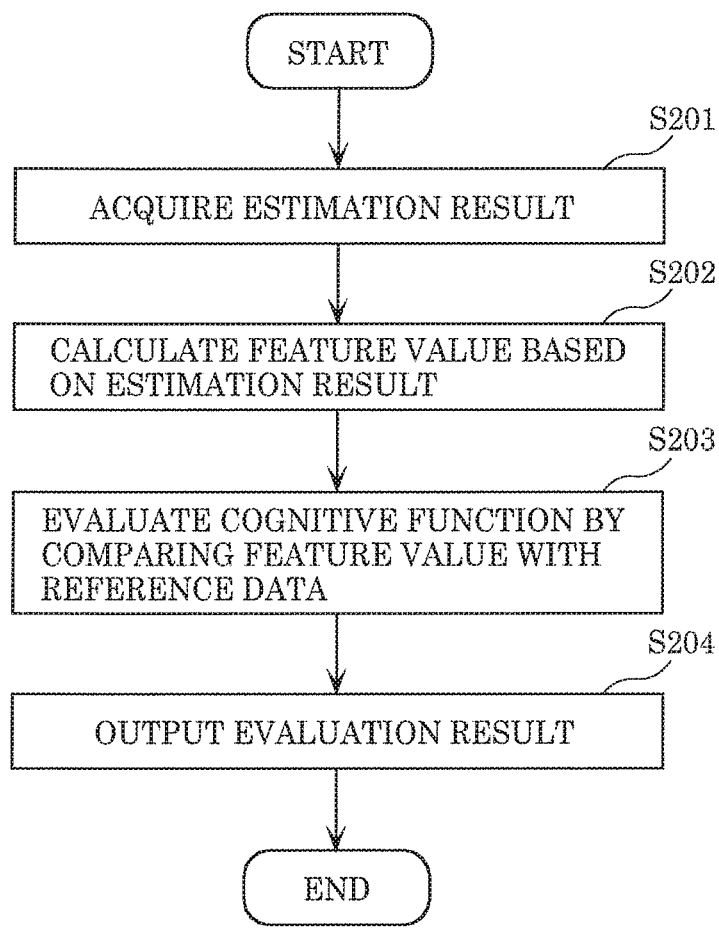

FIG. 9A
| ID | SCORE IN FORGETFULNESS CONSULTATION PROGRAM | OUTSIDE OF ROOM | INSIDE OF ROOM | | |
|---|---|---|---|---|---|
| | | | | ON BED | |
| | | | | STILL | MAKE CHARACTERISTIC MOVEMENT |
| A | 12 | 48.3% | 13.6% | 23.3% | 14.8% |
| B | 12 | 36.9% | 28.4% | 19.1% | 15.6% |
| C | 15 | 36.7% | 19.2% | 25.6% | 18.6% |
| D | 4 | 21.7% | 3.0% | 43.8% | 31.5% |
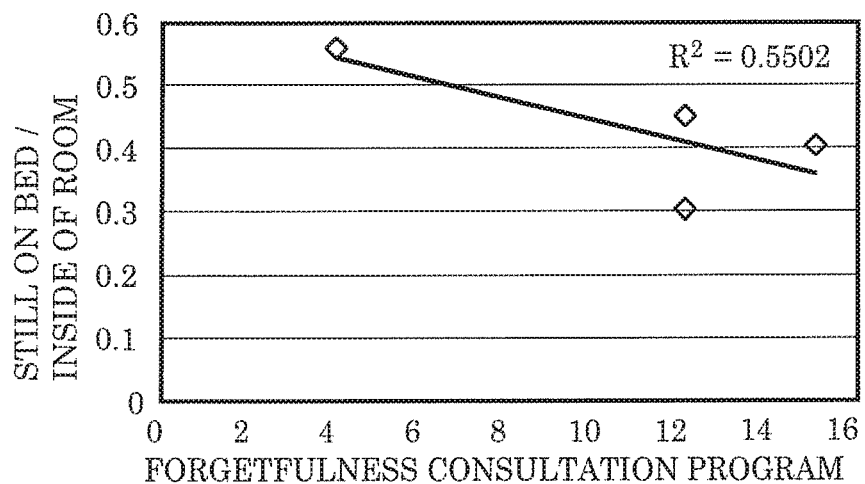
FIG. 9B
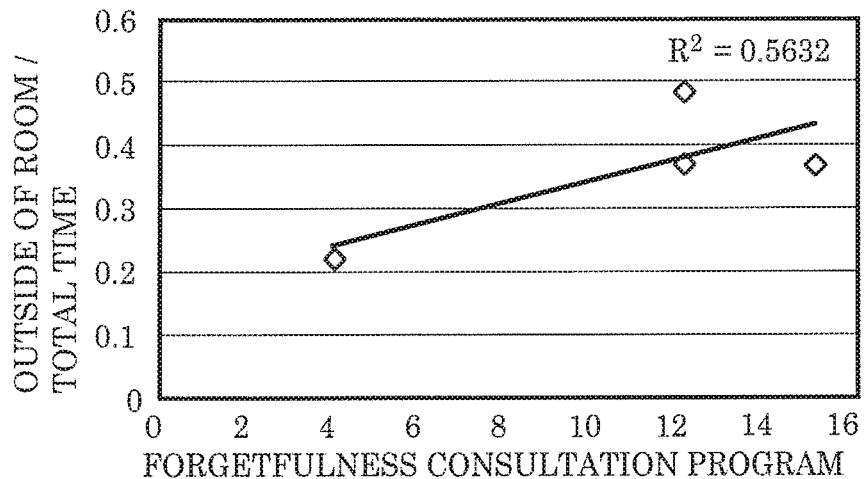
FIG. 9C

COGNITIVE FUNCTION EVALUATION SYSTEM

TECHNICAL FIELD

The present invention relates to an estimation system that estimates at least one of a position and an action of a subject, and a cognitive function evaluation system that evaluates the cognitive function of the subject based on an estimation result obtained from the estimation performed by the estimation system.

BACKGROUND ART

A device is known that detects the movement and the state of a person in a predetermined space such as the entry of the person into a room, or the movement of the person in the room by using an infrared sensor, a microwave, or the like.

Patent Literature 1 discloses a technique in which, in order to estimate the movement and the state of a person, a SVM (support vector machine) is used to perform classification into two categories: whether or not the person is in a room; and whether the person is moving or still in the room.

CITATION LIST

Patent Literature

PTL 1: Japanese Unexamined Patent Application Publication No. 2013-170848

SUMMARY OF THE INVENTION

Technical Problem

However, with the technique disclosed in Patent Literature 1, it is possible to perform classification into two categories: whether or not the person is in a room; and whether the person is moving or still in the room. However, it is not possible to estimate the position of the person in the room or what action the person is doing in the room.

The action of a subject can be estimated by capturing images of the subject by using an image capturing device such as a camera and analyzing the captured images, but, in some cases, it is difficult to capture images from the viewpoint of privacy protection.

The present invention provides an estimation system and the like, with which a position and an action of a subject can be accurately estimated without capturing images.

Solutions to Problem

An estimation system according to an aspect of the present invention includes: a first sensor that detects a first amount of activity that is an amount of activity of a subject in a room; a second sensor that detects a second amount of activity that is an amount of activity of the subject on a bed in the room; and an estimation device that estimates at least one of a position and an action of the subject in association with a position in the room based on the first amount of activity detected by the first sensor and the second amount of activity detected by the second sensor, and outputs an estimation result obtained from the estimation, wherein the first sensor and the second sensor are sensors other than two-dimensional image sensors.

Also, a cognitive function evaluation system according to an aspect of the present invention includes: the above described estimation device; and a cognitive function evaluation device including: an estimation result acquirer that acquires the estimation result obtained from the estimation performed by the estimation device; a calculator that calculates a stay time at a position where the subject is present and an action time of the subject based on the estimation result acquired by the estimation result acquirer, and calculates a feature value based on the stay time and the action time that were calculated; an evaluator that evaluates a cognitive function of the subject based on the feature value calculated by the calculator; and an evaluation result outputter that outputs an evaluation result obtained from the evaluation performed by the evaluator.

The generic or specific aspects of the present invention may be implemented by a system, a method, an integrated circuit, a computer program or a computer readable recording medium such as a CD-ROM, or may be implemented by any combination of a system, a method, an integrated circuit, a computer program, and a recording medium.

Advantageous Effect of Invention

With the estimation system according to an aspect of the present invention, the position and the action of the subject can be accurately estimated without capturing images.

BRIEF DESCRIPTION OF DRAWINGS

FIG. 5B is a diagram showing a table that illustrates the definitions of plots shown in FIG. 5A.

FIG. 8 is a flowchart illustrating a procedure for evaluating the cognitive function of the subject, performed by the cognitive function evaluation system according to Embodiment 2.

FIG. 9A is a diagram showing a table that shows the level of cognitive function and the ratio of position or action of the subject.

FIG. 9B is a diagram showing an example of the ratio of position or action relative to the level of cognitive function of the subject.

FIG. 9C is a diagram showing another example of the ratio of position or action relative to the level of cognitive function of the subject.

DESCRIPTION OF EXEMPLARY EMBODIMENTS

Figure 1:
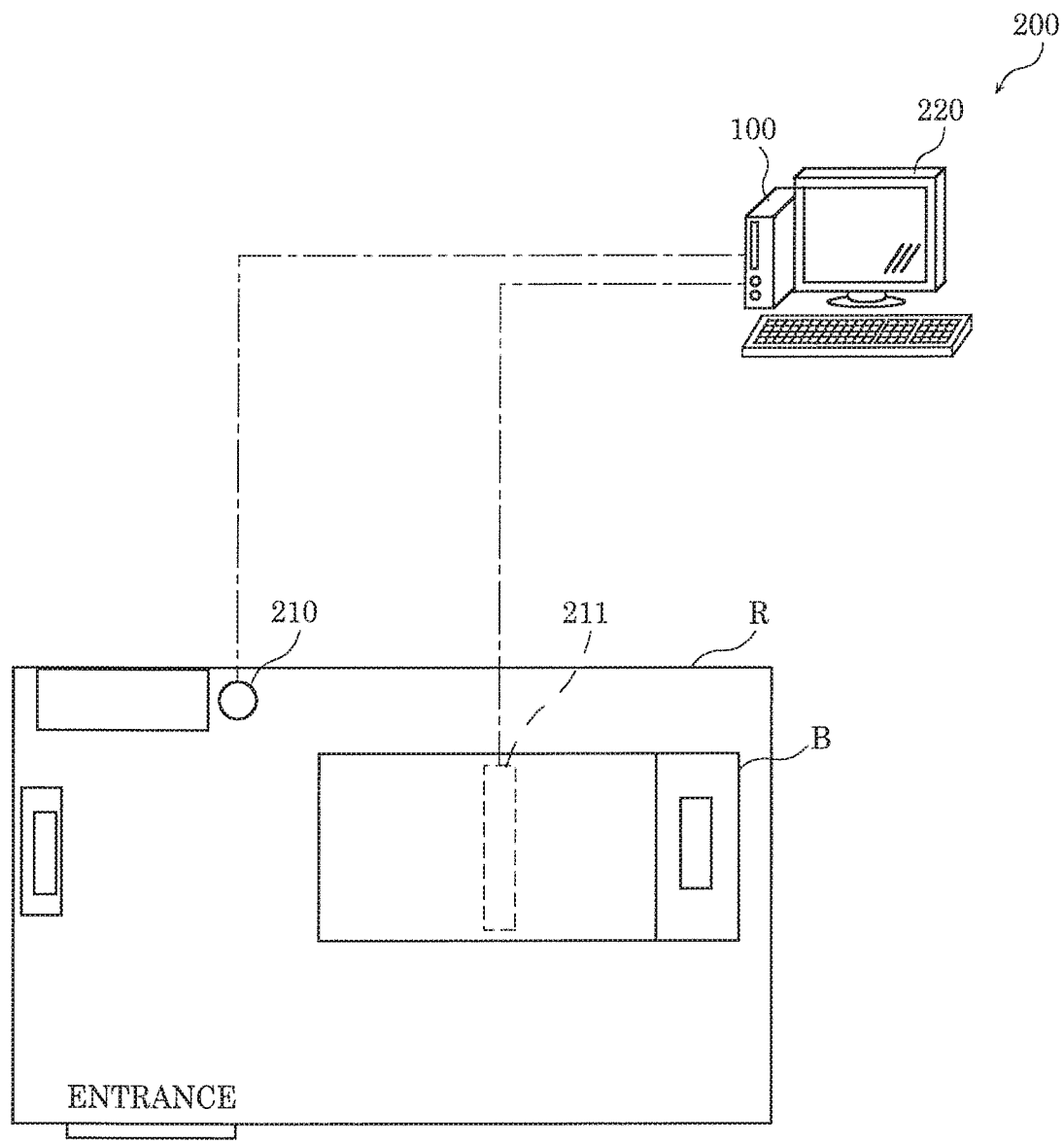
FIG. 1 is a diagram illustrating a configuration of an estimation system according to Embodiment 1.

Hereinafter, embodiments according to the present invention will be described with reference to the drawings. The embodiments described below show generic or specific examples. The numerical values, shapes, materials, structural elements, the arrangement and connection of the structural elements, steps, the order of the steps, and the like shown in the following embodiments are merely examples, and therefore are not intended to limit the scope of the present invention. Also, among the structural elements described in the following embodiments, structural elements not recited in any one of the independent claims are described as arbitrary structural elements.

In addition, the diagrams are schematic representations, and, thus are not necessarily true to scale. Also, in the diagrams, structural elements that are substantially the same are given the same reference numerals, and a redundant description may be omitted or simplified.

Also, in the description given below, the expressions such as "greater than or equal to a threshold value" and "less than or equal to the threshold value" are used, but are not necessarily strict in meaning. For example, the expression "greater than or equal to a threshold value" may mean being greater than the threshold value. Also, in the case where the expressions "greater than or equal to a threshold value" and "less than the threshold value" are used in a comparative manner, they are distinguished by the reference value, and may respectively mean "greater than the threshold value" and "less than or equal to the threshold value".

Embodiment 1

[Configuration of Estimation System]

First, a configuration of an estimation system according to Embodiment 1 will be described with reference to FIGS. 1 and 2.

FIG. 1 is a diagram showing a configuration of estimation system 200 according to Embodiment 1.

Estimation system 200 is a system that estimates the position and the action of a subject by detecting the amounts of activity of the subject in room R. Specifically, estimation system 200 accurately estimates the position and the action of the subject based on the amount of activity of the subject in entire room R (or in other words, in the room) and the amount of activity of the subject on bed B installed in the room. Estimation system 200 is a system for estimating the action of a care receiver who needs to be taken care of, such as an elderly person, in room R where the care receiver performs daily activities.

Estimation system 200 includes first sensor 210, second sensor 211, estimation device 100, and informing device 220.

First sensor 210 is a sensor that detects the amount of activity of the subject in the entire room. First sensor 210 is, for example, a Doppler radio wave sensor, an infrared sensor, or the like. In the case where first sensor 210 is a radio wave sensor, first sensor 210 detects radio wave intensity as a first amount of activity. Also, from the viewpoint of protecting the privacy of the subject, first sensor 210 may be a sensor other than two-dimensional image sensors such as CCD (Charge Coupled Device) and CMOS (Complementary Metal Oxide Semiconductor) that are included in image capturing devices that generate images such as cameras. First sensor 210 detects a first amount of activity that is the amount of activity of the subject in the room, and transmits the detected first amount of activity to estimation device 100.

Second sensor 211 is a sensor that detects the amount of activity of the subject on bed B. Second sensor 211 is, for example, a Doppler radio wave sensor that uses a radio wave of about 24 GHz, an infrared sensor, or the like. FIG. 1 shows a radio wave sensor used as second sensor 211 formed in the form of a sheet provided on bed B. Second sensor 211 detects radio wave intensity as a second amount of activity in the case where second sensor 211 is a radio wave sensor. Also, from the viewpoint of protecting the privacy of the subject, second sensor 211 may be a sensor other than two-dimensional image sensors such as CCD (Charge Coupled Device) and CMOS (Complementary Metal Oxide Semiconductor) that are included in image capturing devices that generate images such as cameras. Second sensor 211 detects the second amount of activity that is the amount of activity of the subject on bed B in the room, and transmits the detected second amount of activity to estimation device 100.

Estimation device 100 is a device that estimates at least one of the position and the action of the subject in association with a position in the room based on the first amount of activity detected by first sensor 210 and the second amount of activity detected by second sensor 211, and outputs an estimation result obtained from the estimation. Estimation, device 100 outputs the estimation result to informing device 220 as information such as sound information or image information. Estimation device 100 is, for example, personal computer, but may be a server device.

Informing device 220 is a device that acquires the estimation result output from estimation device 100, and informs a caregiver who takes care of the subject, a doctor in charge of the subject, and the like of the acquired estimation result. Specifically informing device 220 outputs sound, an image, or the like based on the information indicated by the acquired estimation result such as sound information or image information. Informing device 220 is a device that can output sound, images, or the like, and may be, for example, a speaker, an amplifier, or a display.

First sensor 210 is installed, for example, at a position in room R at which the amount of activity of the subject can be measured. Second sensor 211 is installed, for example, at a position on bed B at which the amount of activity of the subject can be measured. Also, estimation device 100 may be installed in room R, or may be installed in a living room where a caregiver performs daily activities, other activities, and the like. Also, informing device 220 is installed in, for example, the living room in which the caregiver performs daily activities, other activities, and the like.

Figure 2:
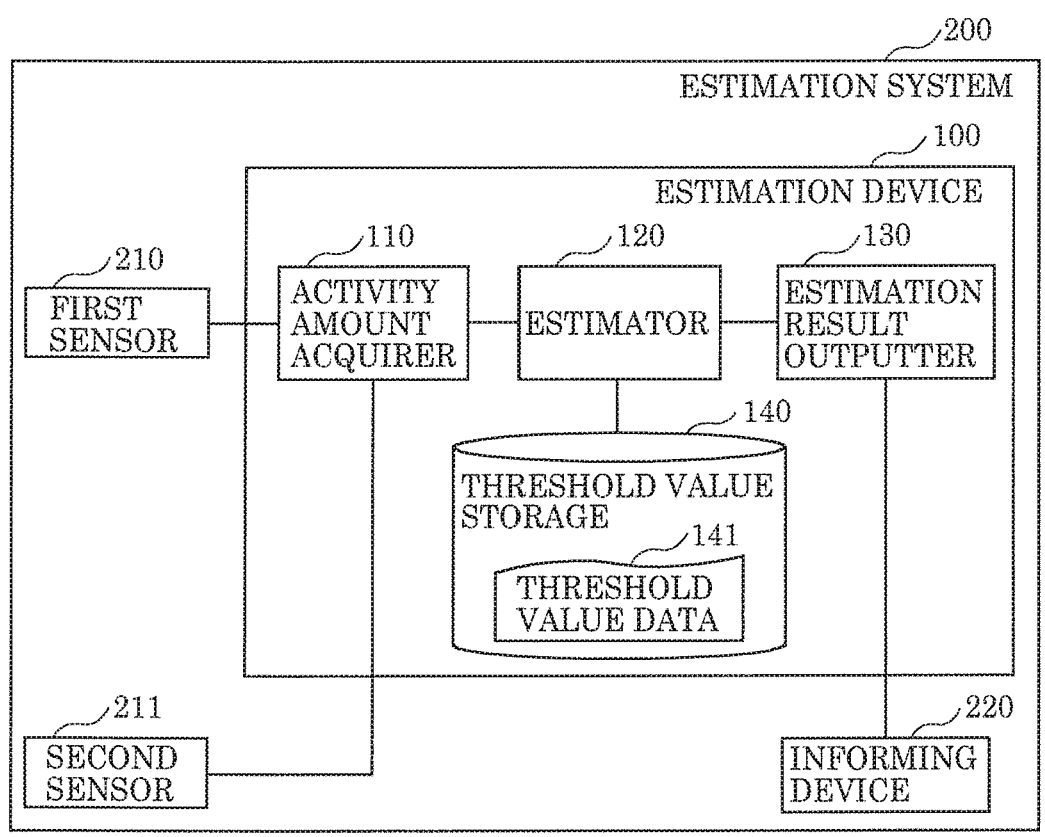
FIG. 2 is a block diagram showing a characteristic functional configuration of the estimation system according to Embodiment 1.

FIG. 2 is a block diagram showing a characteristic functional configuration of estimation system 200 according to Embodiment 1.

As described above, estimation system 200 includes first sensor 210, second sensor 211, estimation device 100, and, informing device 220. Estimation device 100 functionally includes activity amount acquirer 110, estimator 120, estimation result outputter 130, and threshold value storage 140.

Activity amount acquirer 110 is connected to first sensor 210 and second sensor 211 so as to be capable of performing communication, and acquires the first amount of activity from first sensor 210 and also acquires the second amount of activity from second sensor 211. Activity amount acquirer 110 is, for example, an adapter for performing wired communication or wireless communication, or a communication interface such as a communication circuit. Activity amount acquirer 110 may include a plurality of communication interfaces in order to perform communication with first sensor 210 and second sensor 211.

Estimator 120 estimates at least one of the position and the action of the subject in association with a position in the room based on the first, amount of activity and the second amount of activity acquired by activity amount acquirer 110. Specifically, in the case where first sensor 210 and second sensor 211 are radio wave sensors, estimator 120 estimates any one of the following based on a first radio wave intensity that indicates the radio wave intensity detected by first sensor 210 as the first amount of activity and acquired by activity amount acquirer 110 and a second radio wave intensity that indicates the radio wave intensity detected by second sensor 211 as the second amount of activity and acquired by activity amount acquirer 110: (i) the subject is not in the room (or in other words, the subject is outside room R (or in other words, outside of the room)); (ii) the subject is on bed B; (iii) the subject is at a position in the room other than on bed B; and (iv) the subject is making a characteristic movement including a movement of getting off from bed B or a movement of getting into bed B. More specifically, estimator 120 estimates: (i) the subject is not in the room if the first radio wave intensity is less than a first threshold value and the second radio wave intensity is less than a second threshold value; (ii) the subject is at a position in the room other than on bed B if the first radio wave intensity is greater than or equal to the first threshold value and the second radio wave intensity is less than the second threshold value; (iii) the subject is on bed B if the first radio wave intensity is less than the first threshold value and the second radio wave intensity is greater than or equal to the second threshold value; (iv) the subject is making the characteristic movement if the first radio wave intensity is greater than or equal to the first threshold value and the second radio wave intensity is greater than or equal to the second threshold value. The first threshold value and the second threshold value are constants that are determined in advance based on the radio wave detection accuracies of first sensor 210 and second sensor 211, and the like, and are stored in threshold value storage 140 as threshold value data 141.

Estimator 120 is implemented as software by, for example, a control program stored in threshold value storage 140 together with threshold value data 141 and a CPU (Central Processing Unit) that executes the control program. Alternatively, estimator 120 may be implemented as hardware by a dedicated circuit or the like.

Estimation result outputter 130 outputs the estimation result obtained from the estimation performed by estimator 120. In Embodiment 1, estimation result outputter 130 outputs the estimation result obtained from the estimation performed by estimator 120 to informing device 220. Estimation result outputter 130 is, for example, an adapter for performing wired communication or wireless communication, or a communication interface such as a communication circuit.

Threshold value storage 140 is a memory in which threshold value data 141 used by estimator 120 to estimate at least one of the position and the action of the subject is stored. Threshold value storage 140 is implemented by, for example, a memory such as a ROM (Read Only Memory) or a RAM (Random Access Memory), and implemented by a HDD (Hard Disk Drive), a flash memory, or the like.

[Processing Procedure of Estimation System]

Next, a detailed description of the method for estimating the position and the action of the subject performed by estimation system 200 according to Embodiment 1 will be given with reference to FIG. 3.

Hereinafter, an example will be described in which first sensor 210 and second sensor 211 are radio wave sensors.

Figure 3:
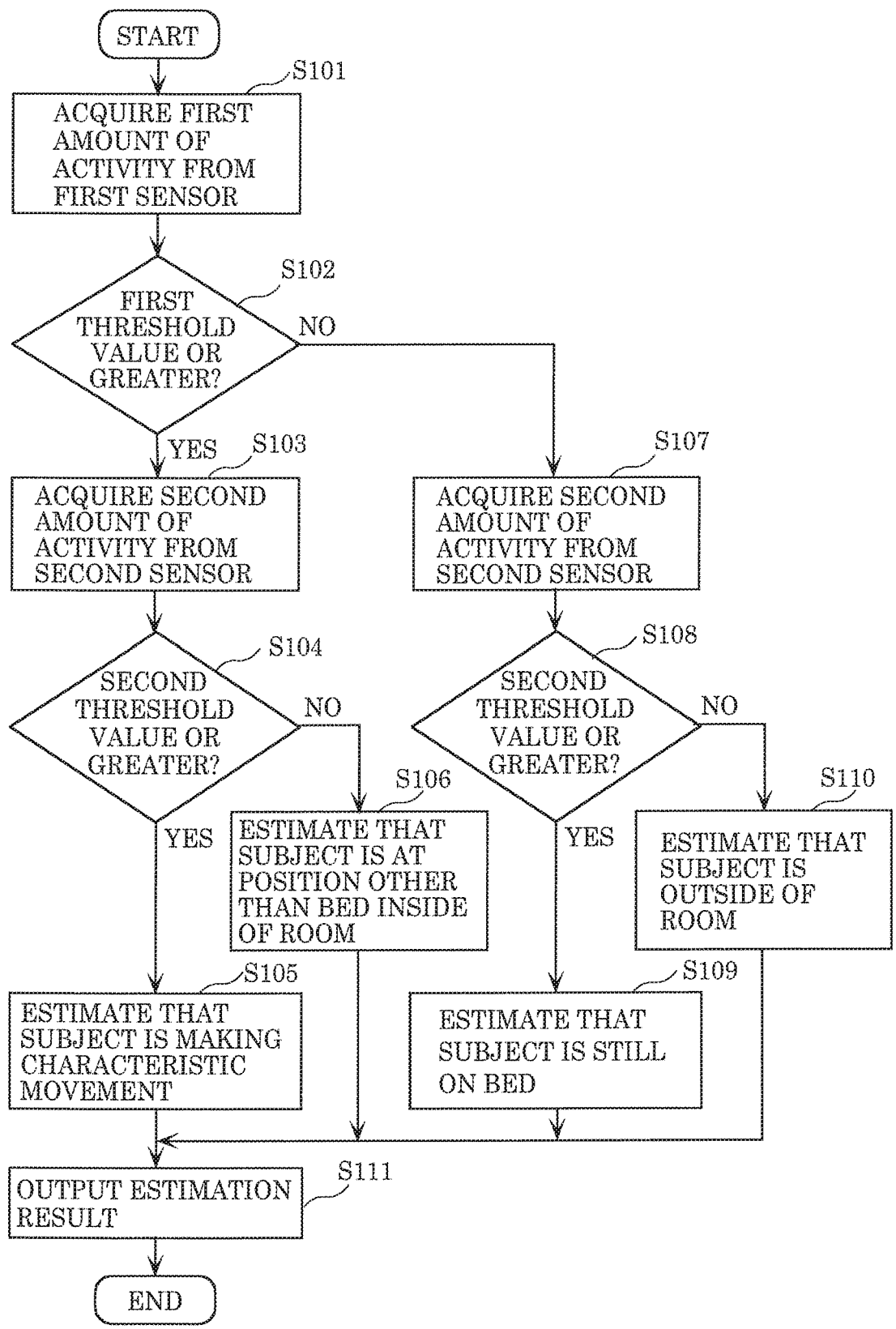
FIG. 3 is a flowchart illustrating a procedure for estimating a position and an action of a subject, performed by the estimation system according to Embodiment 1.

FIG. 3 is a flowchart illustrating a procedure for estimating at least one of the position and the action of the subject, performed by estimation system 200 according to Embodiment 1.

First, activity amount acquirer 110 acquires the first radio wave intensity that indicates the first amount of activity of the subject detected by first sensor 210 (step S101).

Next, estimator 120 determines whether or not the first radio wave intensity acquired by activity amount acquirer 110 is greater than or equal to the first threshold value indicated by threshold value data 141 (step S102).

If it is determined by estimator 120 that the first radio wave intensity acquired by activity amount acquirer 110 is greater than or equal to the first threshold value indicated by threshold value data 141 (Yes in step S102), activity amount acquirer 110 acquires the second radio wave intensity that indicates the second amount of activity of the subject detected by second sensor 211 (step S103).

Next, estimator 120 determines whether or not the second radio wave intensity acquired by activity amount acquirer 110 is greater than or equal to the second threshold value indicated by threshold value data 141 (step S104).

If it is determined that the second radio wave intensity acquired by activity amount acquirer 110 is greater than or equal to the second threshold value indicated by threshold value data 141 (Yes in step S104), estimator 120 estimates that the subject is making the characteristic movement (step S105).

On the other hand, if it is determined that the second radio wave intensity acquired by activity amount acquirer 110 is less than the second threshold value indicated by threshold value data 141 (No in step S104), estimator 120 estimates that the subject is at a position in the room other than on bed B (step S106).

Also, if it is determined by estimator 120 that the first radio wave intensity acquired by activity amount acquirer 110 is less than the first threshold value indicated by threshold value data 141 (No in step S102), activity amount acquirer 110 acquires the second radio wave intensity that indicates the second amount of activity of the subject indicated by second sensor 211 (step S107).

Next, estimator 120 determines whether or not the second radio wave intensity acquired by activity amount acquirer 110 is greater than or equal to the second threshold value indicated by threshold value data 141 (step S108).

If it is determined by estimator 120 that the second radio wave intensity acquired by activity amount acquirer 110 is greater than or equal to the second threshold value indicated by threshold value data 141 (Yes in step S108), estimator 120 estimates that the subject is still on bed B (step S109).

On the other hand, if it is determined by estimator 120 that the second radio wave intensity acquired by activity amount acquirer 110 is less than the second threshold value indicated by threshold value data 141 (No in step S108), estimator 120 estimates that the subject is outside of the room (step S110).

Finally, estimation result outputter 130 outputs an estimation result obtained from the estimation performed by estimator 120 in any of steps S105, S106, S109, and S110 to, for example, informing device 220 (step S111).

[Example of Estimation System]

Next, a detailed description of the processing for estimating at least one of the position and the action of the subject performed by estimation system 200 according to Embodiment 1 will be given with reference to FIGS. 4 to 6.

Figure 4:
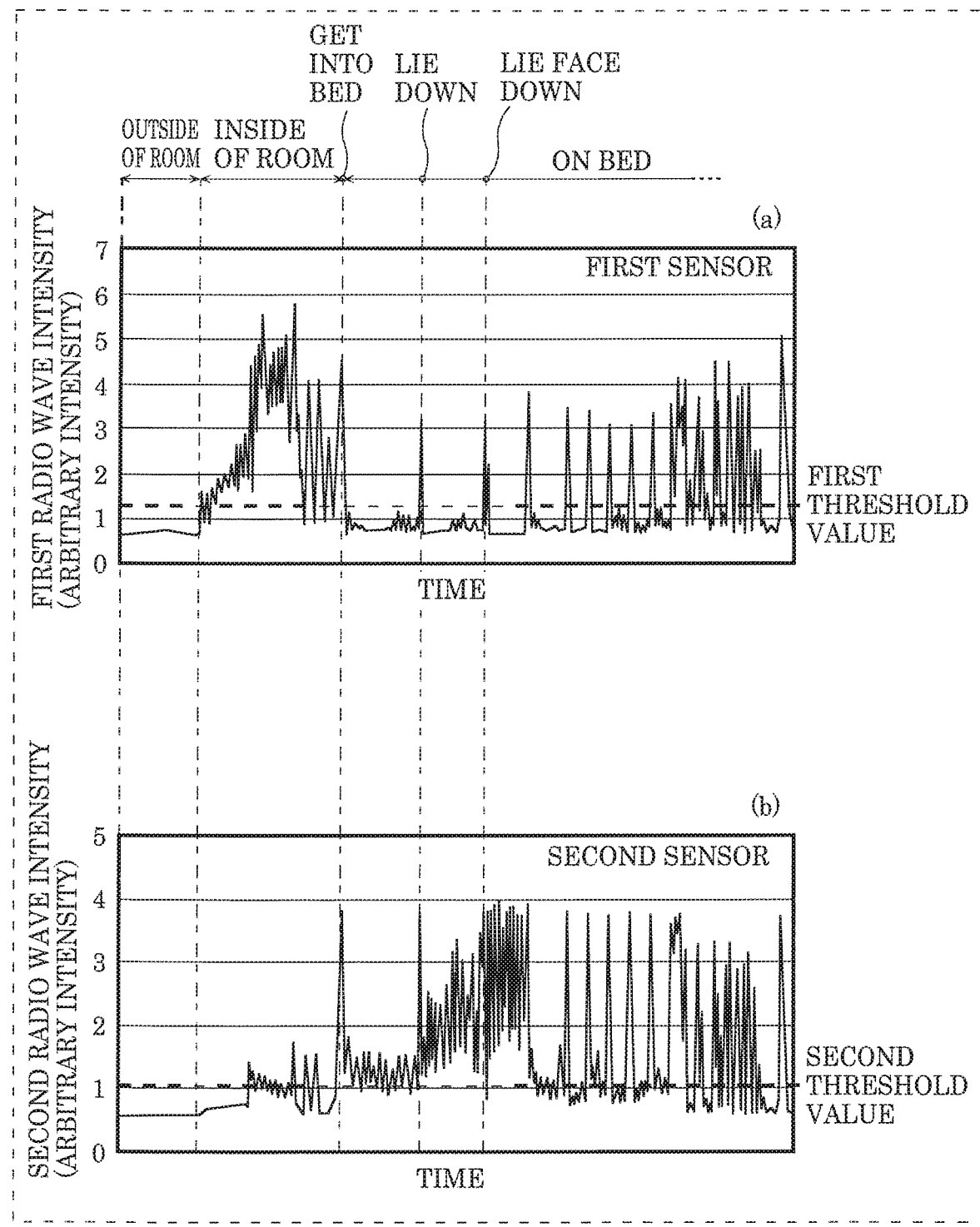
FIG. 4 is a diagram showing an example of variations in radio wave intensities detected by a first sensor and a second sensor.

FIG. 4 is a diagram showing an example of variations in the radio wave intensities detected by first sensor 210 and second sensor 211. Specifically, (a) in FIG. 4 is a graph showing variations in the radio wave intensity detected by first sensor 210 with time, and (b) in FIG. 4 is a graph showing variations in the radio wave intensity detected by second sensor 211 with time. In each of the graphs shown in (a) and (b) of FIG. 4, the horizontal axis represents time, and the time represented by the horizontal axes in the graphs indicate the same time. Specifically, in the graphs shown in (a) and (b) of FIG. 4, the same time is indicated by dash dotted lines.

First, the subject was instructed to be outside of the room. In this case, it can be seen that first sensor 210 and second sensor 211 showed almost no response, with the first radio wave intensity detected by first sensor 210 being less than the first threshold value and the second radio wave intensity detected by second sensor 211 being less than the second threshold value.

Next, the subject was instructed to move from outside of the room to inside of the room. At this time, it can be seen that first sensor 210 detected a first radio wave intensity that was greater than or equal to the first threshold value. On the other hand, it can be seen that second sensor 211 hardly detected a second radio wave intensity that was greater than or equal to the second threshold value.

Next, the subject was instructed to perform a movement of getting into bed B. At this time, it can be seen that first sensor 210 detected a radio wave intensity that was greater than or equal to the first threshold value, and second sensor 211 detected a radio wave intensity that was greater than or equal to the second threshold value. This means that the subject moved within the room and made a significant movement (or in other words, action) on bed B, and thus both first sensor 210 and second sensor 211 detected radio waves greater than the threshold values. That is, as in the case where the subject is instructed to perform a movement of getting off from bed B and moving within the room as indicated by label 17 shown in FIGS. 5A and 5B, which will be described later, first sensor 210 detects a radio wave intensity that is greater than or equal to the first threshold value, and second sensor 211 detects a radio wave intensity that is greater than or equal to the second threshold value (see label 17 shown in FIGS. 5A and 5B).

Next, the subject was instructed to be still on bed B. At this time, it can be seen that first sensor 210 detected a first radio wave intensity that was less than the first threshold value, and second sensor 211 detected a second radio wave intensity that was greater than or equal to the second threshold value.

Next, the subject was instructed to perform a movement of turning over and lying on side on bed B. At this time, it can be seen that first sensor 210 detected a first radio wave intensity that was greater than or equal to the first threshold value, and second sensor 211 detected a second radio wave intensity that was greater than or equal to the second threshold value.

From the foregoing, it can be seen that the position and the action of the subject can be estimated by determining whether or not the first radio wave intensity detected by first sensor 210 is greater than or equal to the first threshold value and whether or not the second radio wave intensity detected by second sensor 211 is greater than or equal to the second threshold value.

Figure 5A:
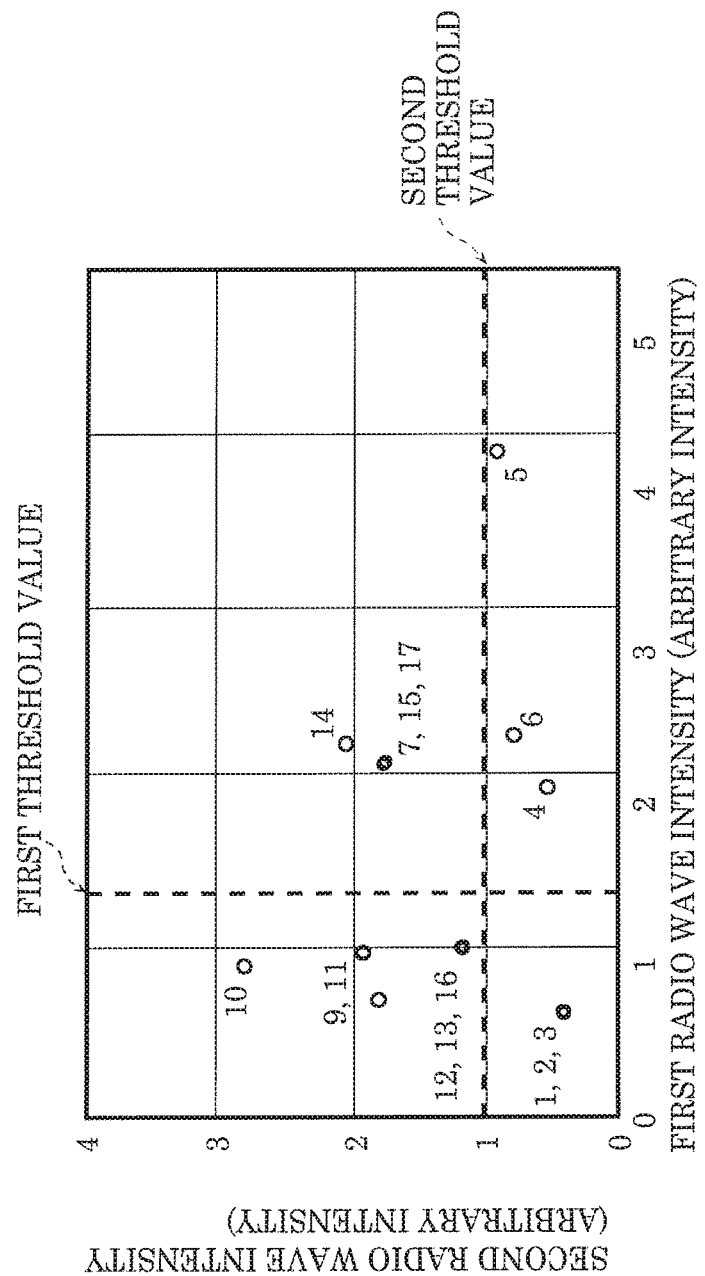
FIG. 5A is a diagram in which the radio wave intensities detected by the first sensor and the second sensor are plotted against predetermined actions of the subject.

FIG. 5A is a diagram showing test results in which the radio wave intensities detected by first sensor 210 and second sensor 211 are plotted against predetermined actions of subjects. FIG. 5B is a diagram showing a table that illustrates the definitions of plots shown in FIG. 5A. The plots shown in FIG. 5A indicate the average value of the first radio wave intensities detected by first sensor 210 and the average value of the second radio wave intensities detected by second sensor 211 in the case where two subjects were instructed to perform actions shown in FIG. 5B. In the graph shown in FIG. 5A, a number assigned to each plot corresponds to a label number shown in FIG. 5B. For example, a plot with a label number "14" shown in FIG. 5A indicates the average value of first radio wave intensities and the average value of second radio wave intensities obtained from the two subjects when the subjects were instructed to perform a movement of getting up on bed B as indicated by the label number "14" shown in FIG. 5B.

Figure 6:
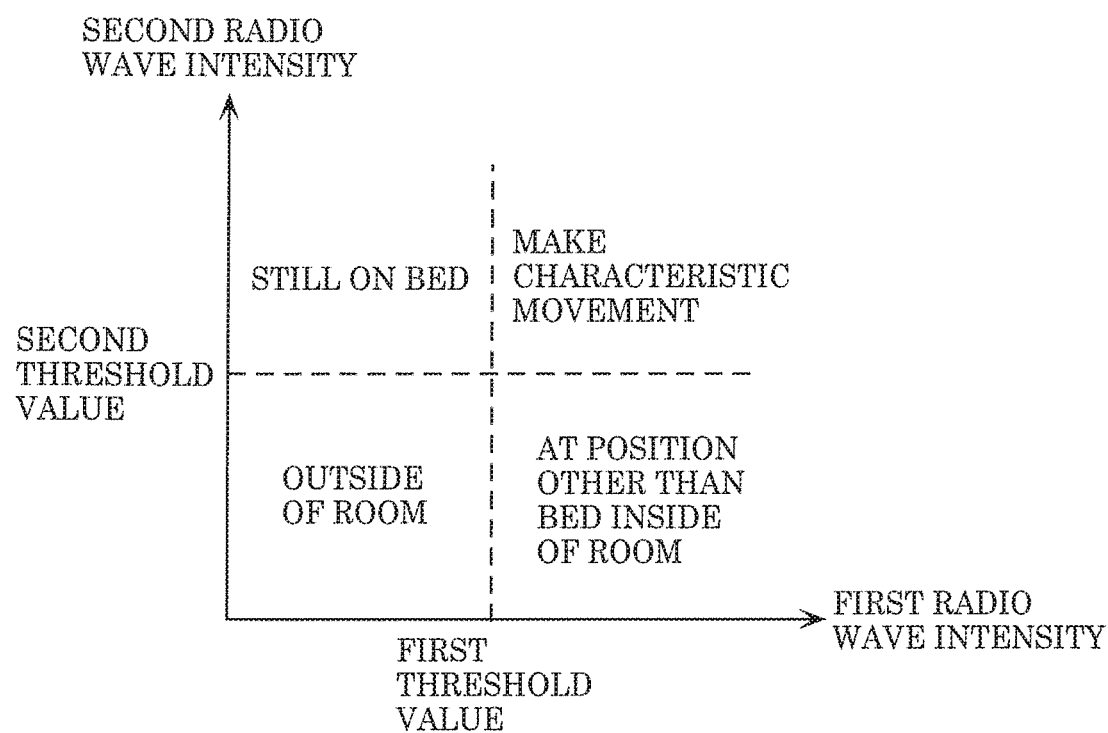
FIG. 6 is a diagram illustrating threshold values used by the estimation system according to Embodiment 1 when estimating the position and the action of the subject.

FIG. 6 is a diagram illustrating threshold values used by estimation system 200 according to Embodiment 1 to estimate the position and the action of the subjects.

It can be seen, from the test results shown in FIGS. 5A and 5B, that at least one of the position and the action of the subject can be estimated based on the first radio wave intensity and the second radio wave intensity. Specifically, as shown in FIG. 6, for example, in a graph with the horizontal axis representing first radio wave intensity and the vertical axis representing second radio wave intensity, when the first threshold value and the second threshold value are defined, at least one of the position and the action of the subject can be estimated by determining in which one of four quadrants defined by the first threshold value and the second threshold value a plot shown in FIG. 5A is positioned. One of the four quadrants indicates that the subject is outside of the room, another quadrant indicates that the subject is at a position in the room other than on bed B, another quadrant indicates that the subject is still on bed B, and another quadrant indicates that the subject is making the characteristic movement. That is, estimator 120 can estimate at least one of the position and the action of the subject based on the first amount of activity detected by first sensor 210 and the second amount of activity detected by second sensor 211.

[Advantageous Effects, Etc.]

As described above, estimation system 200 according to Embodiment 1 includes: first sensor 210 that detects a first amount of activity that is an amount of activity of a subject in a room; second sensor 211 that detects a second amount of activity that is an amount of activity of the subject on bed B in the room; and estimation device 100 that estimates at least one of the position and the action of the subject in association with a position in the room based on the first amount of activity detected by first sensor 210 and the second amount of activity detected by second sensor 211, and outputs an estimation result obtained from the estimation. Also, first sensor 210 and second sensor 211 are sensors other than two-dimensional image sensors.

With the configuration described above, it is possible to accurately estimate, without using images, at least one of the position and the action of the subject in association with a position in the room. Accordingly, with estimation system 200, at least one of the position and the action of the subject can be accurately estimated while protecting the privacy of the subject.

For example, first sensor 210 and second sensor 211 are radio wave sensors.

With the use of radio wave sensors, the movement of the subject in the entire room can be easily detected. Also, the movement of the subject at a specified position such as on bed B can be detected. That is, with the use of radio wave sensors, the amount of activity of the subject at a desired position can be accurately detected with ease.

Also, for example, estimation device 100 estimates any one of the following based on the first radio wave intensity detected by first sensor 210 as the first amount of activity and the second radio wave intensity detected by second sensor 211 as the second amount of activity: (i) the subject is not in the room; (ii) the subject is on bed B; (iii) the subject is at a position in the room other than on bed B; and (iv) the subject is making a characteristic movement including a movement of getting off from bed B or a movement of getting into bed B.

For example, in the case where the subject is a person who needs to be taken care of such as an elderly person, information regarding whether the subject has gotten into bed B or gotten off from bed B is important in taking care of the subject. With the configuration described above, estimation system 200 can accurately estimate the characteristic movement including a movement of getting off from bed B or a movement of getting into bed B.

Also, for example, estimation device 100 estimates that: (i) the subject is not in the room if the first radio wave intensity is less than the first threshold value and the second radio wave intensity is less than the second threshold value; (ii) the subject is at a position in the room other than on bed B if the first radio wave intensity is greater than or equal to the first threshold value and the second radio wave intensity is less than the second threshold value; (iii) the subject is on bed B if the first radio wave intensity is less than the first threshold value and the second radio wave intensity is greater than or equal to the second threshold value; and (iv) the subject is making a characteristic movement if the first radio wave intensity is greater than or equal to the first threshold value and the second radio wave intensity is greater than or equal to the second threshold value.

With the configuration described above, estimation system 200 can easily estimate the position and the action of the subject based on the first threshold value and the second threshold value.

Embodiment 2

Estimation system 200 according to Embodiment 1 is configured to accurately estimate the position and the action of the subject. A cognitive function evaluation system according to Embodiment 2 evaluates the level of cognitive function of the subject by using the an estimation result obtained from estimation performed by estimation device 100 included in estimation system 200.

Hereinafter, the cognitive function evaluation system according to Embodiment 2 will be described. In the description of the cognitive function evaluation system according to Embodiment 2, structural elements that are substantially the same as those of estimation system 200 according to Embodiment 1 are given the same reference numerals, and a redundant description may be omitted or simplified.

[Configuration of Cognitive Function Evaluation System]

A configuration of the cognitive function evaluation system according to Embodiment 2 will be described with reference to FIGS. 2 and 7.

Figure 7:
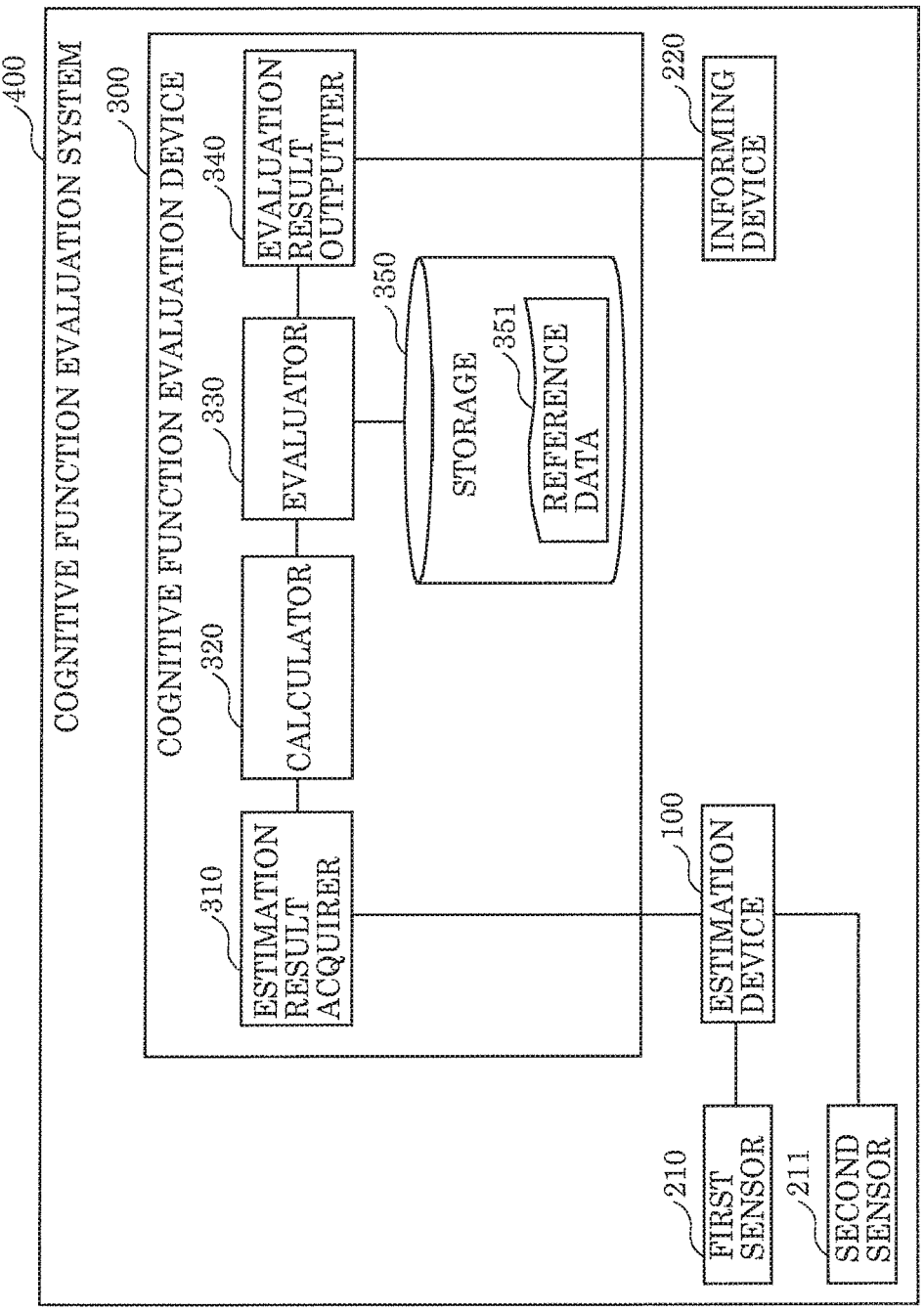
FIG. 7 is a block diagram showing a characteristic functional configuration of a cognitive function evaluation system according to Embodiment 2.

FIG. 7 is a block diagram showing a characteristic functional configuration of cognitive function evaluation system 400 according to Embodiment 2.

Cognitive function evaluation system 400 is a system that evaluates the level of cognitive function of the subject based on an estimation result that indicates at least one of the position and the action of the subject estimated by estimation device 100.

The term "cognitive function" refers to the abilities of recognition, remembering information, making decisions, and the like. Specifically, for example, cognitive function evaluation system 400 performs evaluation to determine whether the subject is a cognitively healthy person whose cognitive function is not impaired, a person suffering from mild cognitive impairment (MCI) (MCI patient), or a person suspected of having dementia (dementia patient).

The term "dementia" refers to symptoms of impairment of the cognitive function. A specific example of dementia is Alzheimer's disease (AD). A person with dementia cannot notice any symptoms of dementia by himself/herself, and thus the dementia patient is convinced and taken to a doctor for a medical examination by a family member or an acquaintance of the dementia patient. Also, for example, whether the evaluatee has dementia can be checked by taking a batch test for diagnosing dementia such as Forgetfulness Consultation Program (available from Nihon Kohden Corporation). MCI indicates symptoms that do not affect daily life although cognitive function impairment is observed. Dementia indicates symptoms that show cognitive function impairment and affect daily life.

The inventors of the present invention found that the estimation results obtained from estimation performed by estimation system 200 show different tendencies between dementia patients and cognitively healthy persons.

As shown in FIG. 7, cognitive function evaluation system 400 includes first sensor 210, second sensor 211, estimation device 100, cognitive function evaluation device 300, and informing device 220.

Estimation device 100 estimates at least one of the position and the action of the subject based on the amounts of activity of the subject detected by first sensor 210 and second sensor 211, and outputs an estimation result obtained from the estimation to cognitive function evaluation device 300. Specifically, estimation result outputter 130 shown in FIG. 2 outputs the estimation result obtained from estimation performed by estimator 120 shown in FIG. 2 to cognitive function evaluation device 300.

Cognitive function evaluation device 300 is a device that acquires the estimation result that indicates at least one of the position and the action of the subject estimated by estimation device 100, and evaluates the level of cognitive function of the subject based on the acquired estimation result. Cognitive function evaluation device 300 is, for example, a personal computer, but may be a server device. Also, estimation device 100 and cognitive function evaluation device 300 may be implemented by a single device such as a personal computer, or may be implemented by a plurality of devices such as personal computers that are connected so as to be capable performing communication. Cognitive function evaluation device 300 outputs, to informing device 220, the evaluation result regarding the cognitive function of the evaluated subject as information such as sound information or image information.

Informing device 220 outputs sound, an image, or the like based on the information indicated by the evaluation result acquired from cognitive function evaluation device 300 such as sound information or image information.

Cognitive function evaluation device 300 functionally includes estimation result acquirer 310, calculator 320, evaluator 330, evaluation result outputter 340, and storage 350.

Estimation result acquirer 310 acquires the estimation result obtained from the estimation performed by estimation device 100. Specifically, estimation result acquirer 310 acquires the estimation result output by estimation result outputter 130.

Estimation result acquirer 310 is, for example, an adapter for performing wired communication or wireless communication, or a communication interface such as a communication circuit, in order to connect to estimation result outputter 130 of estimation device 100 so as to be capable of performing communication.

Calculator 320 calculates a stay time at a position where the subject stays and action time of the subject based on the estimation result acquired by estimation result acquirer 310, and calculates the feature value based on the stay time and the action time that were calculated. A specific method for calculating the feature value will be described later.

Estimation result acquirer 310 may acquire time information associated with the estimation result by incorporating the time information in the estimation result. That is, in this case, estimator 120 included in estimation device 100 associates time information that indicates the time at which at least one of the position and the action of the subject is performed, when estimating at least one of the position and the action of the subject, and estimates as an estimation result. Estimation result outputter 130 outputs the estimation result incorporating the time information to estimation result acquirer 310. In this case, estimation device 100 may include a timer (not shown) for measuring time such as a real time clock (RTC). Also, cognitive function evaluation device 300 may include a timer (not shown) such as an RTC, and calculator 320 may associate a result of measuring time performed by the timer with the estimation result acquired by estimation result acquirer 310.

For example, calculator 320 calculates the time during which the subject is still on bed B relative to the time during which the subject is in the room as the feature value. As used herein, the expression "being in the room" means being on bed B as well as being at a position other than on bed B.

Also, for example, calculator 320 calculates the time during which the subject is not in the room (or in other words, the time during which the subject is outside of the room) as the feature value.

Calculator 320 is implemented as software by, for example, a control program stored in storage 350 and a CPU that executes the control program. Alternatively, calculator 320 may be implemented as hardware by a dedicated circuit or the like.

Evaluator 330 evaluates the cognitive function of the subject based on the feature values calculated by calculator 320. Specifically, evaluator 330 evaluates the cognitive function of the subject by comparing the feature value calculated by calculator 320 with reference data 351 stored in storage 350. For example, in storage 350, threshold values for the feature values for specifying the level of cognitive function with which it is possible to distinguish a cognitively healthy person or an MCI patient from a dementia patient are stored as reference data 351. Evaluator 330 evaluates the level of dementia by comparing the feature value calculated by calculator 320 with the threshold value stored in reference data 351.

Evaluator 330 is implemented as software by, for example, a control program stored in storage 350 and a CPU that executes the control program. Alternatively, evaluator 330 may be implemented as hardware by a dedicated circuit or the like.

Calculator 320, evaluator 330, and estimator 120 that is included in estimation device 100 (see FIG. 2) may be implemented by individual processors, microcomputers, or dedicated circuits that have their functions, or may be implemented by a combination of two or more of a processor, a microcomputer, or a dedicated circuit.

Evaluation result outputter 340 outputs an evaluation result that indicates the level of cognitive function of the subject evaluated by evaluator 330. Evaluation result outputter 340 outputs, for example, the evaluation result of evaluator 330 to informing device 220 as image data. Informing device 220 acquires the image data output by evaluation result outputter 340, and displays an image based on the acquired image data. The evaluation result of evaluator 330 may be output from evaluation result outputter 340 as sound data.

Evaluation result outputter 340 is, for example, an adapter for performing wired communication or wireless communication, or a communication interface such as a communication circuit. Informing device 220 acquires the estimation result output from evaluation result outputter 340, and provides information indicating the acquired evaluation result to a caregiver or the like via sound, an image, or the like.

Storage 350 is a memory in which reference data 351 indicating the relationship between the feature value of people and the cognitive function of the people is stored. Storage 350 is, for example, a memory such as a ROM, and implemented by a HDD, a flash memory, or the like. A detailed description of reference data 351 will be given later.

Storage 350 and threshold value storage 140 (see FIG. 2) may be implemented by a single memory such as a HDD. In the memory, control programs that are respectively executed by threshold value data 141, reference data 351, estimation device 100, and cognitive function evaluation device 300, and the like may be stored.

[Processing Procedure of Cognitive Function Evaluation System]

Next, a detailed description of the method for evaluating the cognitive function of the subject executed by cognitive function evaluation system 400 according to Embodiment 2 will be given with reference to FIG. 8.

FIG. 8 is a flowchart illustrating a procedure for evaluating the cognitive function of the subject, performed by cognitive function evaluation system 400 according to Embodiment 2.

First, estimation result acquirer 310 acquires, from estimation device 100, an estimation result obtained from estimation of at least one of the position and the action of the subject associated with room R (step S201).

Next, calculator 320 calculates a stay time at a position where the subject is present and an action time of the subject based on the estimation result acquired by estimation result acquirer 310, and calculates the feature value of the subject based on the stay time and the action time that were calculated (step S202).

Next, evaluator 330 evaluates the level of cognitive function of the subject based on the feature value of the subject calculated by calculator 320 (step S203). In step S203, evaluator 330 evaluates the cognitive function of the subject by, specifically, comparing the feature value of the subject calculated by calculator 320 with reference data 351.

Finally, evaluation result outputter 340 outputs, to informing device 220, the evaluation result obtained as a result of evaluator 330 performing evaluation (step S204). Informing device 220 informs the evaluation result output from evaluation result outputter 340.

[Example of Cognitive Function Evaluation System]

Next, a detailed description of results of calculation of the feature value of the subject executed by cognitive function evaluation system 400 according to Embodiment 2 will be given with reference to FIGS. 9A to 9C. "Inside of room" shown in FIGS. 9A and 9B encompasses the case where the subject is on bed B.

FIG. 9A is a diagram showing a table that shows the level of cognitive function and the ratio of position or action of the subject.

To diagnose dementia, a person can take a batch test for diagnosing dementia such as "Forgetfulness Consultation Program", whereby whether or not the person has dementia can be determined. FIG. 9A shows the scores of the Forgetfulness Consultation Program obtained as a result of four subjects (specifically, four people with IDs of A, B, C, and D shown in FIG. 9A) taking the Forgetfulness Consultation Program and the estimation results obtained from estimation performed by estimation device 100. The position and the action of the subject indicated by each estimation result is any one of (i) being outside of the room, (ii) being at a position in the room other than on bed, (iii) being still on bed, and (iv) making a characteristic movement as shown in FIG. 6. The test period was 6 months, and estimation device 100 performed estimation every 15 minutes to determine any one of the following: (i) the subject was outside of the room, (ii) the subject was at a position in the room other than on bed, (iii) the subject was still on bed, and (iv) the subject was making a characteristic movement. The estimation results obtained from estimation performed by estimation device 100 were stored in storage 350 included in cognitive function evaluation system 400, and calculator 320 included in cognitive function evaluation device 300 calculated the stay time at a position where the subject was present and the action time of the subject based on the estimation results stored in storage 350, and calculated the feature value based on the stay time and the action time that were calculated.

As shown in FIG. 9A, the subject with an ID of A (referred to as subject A) exhibited a score of 12 in the Forgetfulness Consultation Program. Also, the subject with an ID of B (referred to as subject B) exhibited a score of 12 in the Forgetfulness Consultation Program. The subject with an ID of C (referred to as subject C) exhibited a score of 15 in the Forgetfulness Consultation Program. The subject with an ID of D (referred to as subject D) exhibited a score of 4 in the Forgetfulness Consultation Program. In Forgetfulness Consultation Program, a subject with a score less than or equal to 9 is diagnosed as a dementia patient, a subject with a score of 10 to 12 is diagnosed as an MCI patient, and a subject with a score greater than or equal to 13 is diagnosed as a cognitively healthy person. That is, from the scores in the Forgetfulness Consultation Program, it can be seen that subjects A and B are MCI patients, subject; C is a cognitively healthy person, and subject D is a dementia patient with cognitive function impairment.

It can be seen that, with subjects A to C, the ratio of time spent outside of the room was higher, and the ratio of time spent on bed B was lower even when they were in the room, as compared with subject D.

FIG. 9B is a diagram showing an example of the ratio of position or action relative to the level of cognitive function of the subject. In the graph shown in FIG. 9B, the horizontal axis represents the score in the Forgetfulness Consultation Program, and the vertical axis represents the ratio of the time during which the subject is still on bed relative to the time during which the subject is in the room. More specifically, the vertical axis of the graph shown in FIG. 9B represents the ratio of the time during which the subject is on bed B relative to the sum of the time spent at three positions or spent to perform three actions out of the four quadrants shown in FIG. 6, the three positions or actions including: being at a position in the room other than on bed B; being still on bed B; and making a characteristic movement. Also, the correlation coefficient shown in FIG. 9B was 0.5502.

It can be seen from FIG. 9B that the smaller the score in the Forgetfulness Consultation Program, the larger the ratio of the time during which the subject is still on bed relative to the time during which the subject is in the room. This is presumably because the motivation for taking an action decreases as the level of cognitive impairment of the subject is lower, and thus the subject tends to spend time lazily on bed B when the subject is in the room.

From the results shown in FIG. 9B, for example, if the ratio of the time during which the subject is still on bed relative to the time during which the subject is in the room is greater than or equal to 0.5, it is estimated that the subject is a dementia patient with cognitive function impairment. If the ratio of the time during which the subject is still on bed relative to the time during which the subject is in the room is less than 0.5, it is estimated that the subject is a cognitively healthy person whose cognitive function is not impaired or an MCI patient.

For example, calculator 320 calculates the ratio of the time during which the subject is still on bed relative to the time during which the subject is in the room as the feature value. Also, for example, storage 350 stores therein a threshold value (for example, 0.5) for the ratio of the time during which the subject is still on bed relative to the time during which the subject is in the room, as reference data 351. By doing so, evaluator 330 can evaluate the level of cognitive function of the subject based on, for example, the feature value calculated by calculator 320 and reference data 351 stored in storage 350.

FIG. 9C is a diagram showing another example of the ratio of position or action relative to the level of cognitive function of the subject.

In the graph shown in FIG. 9C, the horizontal axis represents the score in the Forgetfulness Consultation Program, and the vertical axis represents the ratio of the time during which the subject is outside of the room relative to the total time in the test period. Also, the correlation coefficient shown in FIG. 9C was 0.5632.

It can be seen from FIG. 9C that the smaller the score in the Forgetfulness Consultation Program, the lower the ratio of the time during which the subject is outside of the room relative to the total time in the test period. This is presumably because the motivation for taking an action decreases as the level of cognitive impairment of the subject is lower, and thus the subject does not go outside of the room.

From the results shown in FIG. 9C, for example, if the ratio of the time during which the subject is outside of the room relative to the total time in the test period is less than 0.3, it is estimated that the subject is a dementia patient with cognitive function impairment. If the ratio of the time during which the subject is outside of the room relative to the total, time in the test period is greater than or equal to 0.3, it is estimated that the subject is a cognitively healthy person whose cognitive function is not impaired, or an MCI patient.

For example, calculator 320 calculates the ratio of the time during which the subject is outside of the room relative to the total time in the test period as the feature value. Also, for example, storage 350 stores therein a threshold value (for example, 0.3) for the ratio of the time during which the subject is outside of the room relative to the total time in the test period, as reference data 351. By doing so, evaluator 330 can evaluate the level of cognitive function of the subject based on, for example, the feature value calculated by calculator 320 and reference data 351 stored in storage 350.

In the case where the test period for estimation results used by calculator 320 to calculate the feature value has been determined in advance, for example, time may be used as reference data 351. For example, calculator 320 may calculate the time during which the subject is outside of the room (or in other words, the time during which the subject is not in the room) as the feature value. That is, calculator 320 may calculate the feature value based on the time during which the subject is not in the room.

In the example given above, the test period is set to 6 months, but there is no particular limitation on the test period. For example, the test period may be 1 week, or may be 1 month. The test period may be shorter than 1 week, or may be longer than 6 months.

[Advantageous Effects, Etc.]

As described above, cognitive function evaluation system 400 according to Embodiment 2 includes estimation device 100 and cognitive function evaluation device 300 that includes: estimation result acquirer 310 that acquires an estimation result obtained from estimation performed by estimation device 100; calculator 320 that calculates a stay time at a position where a subject is present and an action time of the subject based on the estimation result acquired by estimation result acquirer 310, and calculates a feature value based on the stay time and the action time that were calculated; evaluator 330 that evaluates the cognitive function of the subject based on the feature value calculated by calculator 320; and evaluation result outputter 340 that outputs an evaluation result obtained from the evaluation performed by evaluator 330.

With the configuration described above, cognitive function evaluation system 400 can accurately evaluate the level of cognitive function of the subject based on the estimation result obtained from the estimation performed by estimation device 100.

For example, calculator 320 calculates the time during which the subject is still on bed B relative to the time during which the subject is in the room as the feature value. As used herein, the expression "being in the room" means being on bed B as well as being at a position other than on bed B.

With the configuration described above, the level of cognitive function of the subject can be evaluated easily and with higher accuracy based on the estimation result obtained from the estimation performed by estimation device 100.

Also, for example, calculator 320 calculates the time during which the subject is not in the room as the feature value.

With this configuration as well, the level of cognitive function of the subject can be evaluated easily and with higher accuracy based on the estimation result obtained from the estimation performed by estimation device 100.

Also, for example, cognitive function evaluation system 400 further includes storage 350 in which reference data 351 that indicates the relationship between the feature value of people and the cognitive function of the people is stored. In this case, for example, evaluator 330 evaluates the cognitive function of the subject by comparing the feature value of the subject calculated by calculator 320 with reference data 351.

That is, cognitive function evaluation system 400 may evaluate the cognitive function of the subject by performing communication with an external server device or the like in which reference data 351 is stored, but may include storage 350 that is a storage device in which reference data 351 is stored. With this configuration, cognitive function evaluation system 400 can evaluate the cognitive function of the subject without connecting to a network for performing communication with an external server device. Accordingly, the usability of cognitive function evaluation system 400 is improved.

Also, for example, cognitive function evaluation system 400 further includes informing device 220 that informs the evaluation result output from evaluation result outputter 340.

With the configuration described above, it is possible to easily inform the subject; of the evaluation result obtained from the evaluation performed by cognitive function evaluation device 300.

Other Embodiments

Estimation system 200 according to Embodiment 1, cognitive function evaluation system 400 according to Embodiment 2, and the like have been described above, but the present invention is not limited to the embodiments given above.

For example, in the embodiments given above, estimator 120 included in estimation device 100, as well as the processing units included in cognitive function evaluation device 300 such as calculator 320 and evaluator 330 are implemented as software by the processors executing programs. However, the present invention is not limited to such an implementation method. The processing units may be implemented as hardware by using dedicated electronic circuits that use gate arrays and the like.

Also, in the embodiments given above, as a specific example of cognitive function evaluation, cognitive function evaluation device 300 is configured to evaluate whether or not the subject has dementia. However, the evaluation performed by cognitive function evaluation device 300 of the present embodiment; is not limited to evaluating whether or not the subject has dementia. Cognitive function evaluation device 300 may evaluate, for example, the degree of intoxication of the subject.

In the example shown in FIGS. 9A to 9C, a cognitively healthy person (subject C) was not distinguished from MCI patients (subjects A and B), but a cognitively healthy person may be distinguished from an MCI patient by performing a plurality of examinations. In this case, cognitive function evaluation device 300 may evaluate whether the subject is a cognitively healthy person, an MCI patient, or a dementia patient.

Also, in the embodiments given above, Alzheimer's disease is given as a specific example of a symptom of cognitive function impairment. Here, the term "cognitive function" refers to the abilities of recognition, remembering information, making decisions, and the like, and the term "dementia" refers to symptoms of impairment of the cognitive function. That is, the cognitive function evaluated by cognitive function evaluation device 300 is not limited to Alzheimer's disease, and may be, for example, vascular dementia or the like.

Also, in the embodiments given above, in order to evaluate the cognitive function of the subject, data that indicates the relationship between the score in the Forgetfulness Consultation Program and the estimation results regarding the position and the action of the subject has been stored in advance in storage 350 as reference data 351. Reference data 351 is not limited to the data that indicates the relationship between the score in the Forgetfulness Consultation Program and the estimation results, and may be any data as long as it is possible to evaluate the cognitive function by comparing with the estimation result regarding the position and the action of the subject. For example, reference data 351 may be data that indicates the relationship between the score in MoCA (Montreal Cognitive Evaluation) test or the score in MMSE (Mini-Mental State Examination) and the estimation result regarding the position and the action of the subject.

Also, the present invention may be implemented as a method executed by estimation system 200 according to the embodiment given above. That is, the present invention may be implemented as an estimation method that includes: detecting a first amount of activity that is an amount of activity of a subject in a room by using first sensor 210 that is a sensor other than a two-dimensional image sensor and detecting a second amount of activity that is an amount of activity of the subject on bed B in the room by using second sensor 211 that is a sensor other than a two-dimensional image sensor; estimating at least one of a position and an action of the subject in association with a position in the room based on the first amount of activity detected by first sensor 210 and the second amount of activity detected by second sensor 211; and outputting an estimation result obtained from the estimating.

Also, the present invention may be implemented as a method executed by cognitive function evaluation system 400 according to the embodiment given above. That is, the present invention may be implemented as a cognitive function evaluation, method that is executed by a computer, the method including: detecting a first amount of activity that is an amount of activity of a subject in a room by using first sensor 210 that is a sensor other than a two-dimensional image sensor and detecting a second amount of activity that is an amount of activity of the subject on bed B in the room by using second sensor 211 that is a sensor other than a two-dimensional image sensor; estimating at least one of a position and an action of the subject in association with a position in the room based on the first amount of activity detected by first sensor 210 and the second amount of activity detected by second sensor 211; calculating a stay time at a position where the subject is present and an action time of the subject based on an estimation result obtained from the estimation performed in the estimating and calculating a feature value based on the stay time and the action time that were calculated; evaluating a cognitive function of the subject based on the feature value calculated in the calculating; and outputting an evaluation result obtained from the evaluation performed in the evaluating.

Also, the present invention may be implemented as a program that causes a computer to execute the steps of the above-described estimation method or the above-described cognitive function evaluation method. In other words, the present invention may be implemented as a program that causes a computer to execute the steps executed by the cognitive function evaluation device. Also, the present invention may be implemented as a computer readable recording medium, such as a CD-ROM, in which the above-described program is recorded. Also, the present invention may be implemented as information, data or a signal that indicates the above-described program. The program, the information, the data, and the signal may be distributed via a communication network such as the Internet.

With this configuration, the estimation method can be executed by a computer as a program with which the position and the action of the subject can be accurately estimated without capturing images. Also, the cognitive function evaluation method can be executed by a computer as a program with which the cognitive function of the subject can be accurately evaluated.

The present invention also encompasses other embodiments obtained by making various modifications that can be conceived by a person having ordinary skill in the art to the above embodiments as well as embodiments implemented by any combination of the structural elements and the functions of the above embodiments without departing from the scope of the present invention.

The invention claimed is:

1. A cognitive function evaluation system, comprising:
a first sensor that detects a first amount of activity that is an amount of activity of a subject in a room;
a second sensor that detects a second amount of activity that is an amount of activity of the subject on a bed in the room; and
an estimation device that estimates at least one of a position and an action of the subject in association with a position in the room based on the first amount of activity detected by the first sensor and the second amount of activity detected by the second sensor, and outputs an estimation result obtained from the estimation,
wherein the first sensor and the second sensor are radio wave sensors,
the cognitive function evaluation system further comprises a cognitive function evaluation device including:
an estimation result acquirer that acquires a plurality of estimation results over time, obtained from the estimation performed by the estimation device;
a calculator that calculates a feature value as a result of at least one of the estimation results acquired by the estimation result acquirer;
an evaluator that evaluates a cognitive function of the subject based on the feature value calculated by the calculator; and
an evaluation result outputter that outputs an evaluation result obtained from the evaluation performed by the evaluator, and
wherein the estimation device is configured to estimate, as each estimation result, a corresponding one of the following based on a first radio wave intensity detected by the first sensor as the first amount of activity and a second radio wave intensity detected by the second sensor as the second amount of activity:
(i) the subject is not in the room,
(ii) the subject is on the bed,
(iii) the subject is at a position in the room other than on the bed, and
(iv) the subject is making a characteristic movement including a movement of getting off from the bed or a movement of getting into the bed,
wherein the estimation device estimates that:
(i) the subject is not in the room when the first radio wave intensity is less than a first threshold value and the second radio wave intensity is less than a second threshold value;
(ii) the subject is at a position in the room other than on the bed when the first radio wave intensity is greater than or equal to the first threshold value and the second radio wave intensity is less than the second threshold value;
(iii) the subject is on the bed when the first radio wave intensity is less than the first threshold value and the second radio wave intensity is greater than or equal to the second threshold value; and
(iv) the subject is making the characteristic movement when the first radio wave intensity is greater than or equal to the first threshold value and the second radio wave intensity is greater than or equal to the second threshold value, wherein the second threshold value is less than the first threshold value.

2. The cognitive function evaluation system according to claim 1, further comprising a storage in which reference data that indicates a relationship between the feature value of people and a cognitive function of the people is stored, wherein the evaluator evaluates the cognitive function of the subject by comparing the feature value of the subject calculated by the calculator with the reference data.

3. The cognitive function evaluation system according to claim 1, further comprising an informing device that provides information indicating the evaluation result output from the evaluation result outputter.

4. A non-transitory computer-readable recording medium for use in a computer, the recording medium having a computer program recorded thereon for causing the computer to execute a cognitive function evaluation method including:

detecting, by a first sensor, a first amount of activity that is an amount of activity of a subject in a room, and detecting, by a second sensor, a second amount of activity that is an amount of activity of the subject on a bed in the room;

estimating at least one of a position and an action of the subject in association with a position in the room based on the first amount of activity detected by the first sensor and the second amount of activity detected by the second sensor;

calculating a feature value as a result of at least one estimation result obtained from the estimating;

evaluating a cognitive function of the subject based on the feature value calculated in the calculating; and outputting an evaluation result obtained in the evaluating, the first sensor and the second sensor are radio wave sensors, the estimating includes estimating, as each estimating result, a corresponding one of the following based on a first radio wave intensity detected by the first sensor as the first amount of activity and a second radio wave intensity detected by the second sensor as the second amount of activity:

(i) the subject is not in the room when the first radio wave intensity is less than a first threshold value and the second radio wave intensity is less than a second threshold value;

(ii) the subject is at a position in the room other than on the bed when the first radio wave intensity is greater than or equal to the first threshold value and the second radio wave intensity is less than the second threshold value;

(iii) the subject is on the bed when the first radio wave intensity is less than the first threshold value and the second radio wave intensity is greater than or equal to the second threshold value; and (iv) the subject is making a characteristic movement when the first radio wave intensity is greater than or equal to the first threshold value and the second radio wave intensity is greater than or equal to the second threshold value, the characteristic movement including a movement of getting off from the bed or a movement of getting into the bed, and the second threshold value is less than the first threshold value.

* * * * *